United States Patent [19]

Schwan

[11] 4,001,269

[45] Jan. 4, 1977

[54] 3-AMINO-5,6-DIMETHOXYINDAZOLE HYDROCHLORIDE

[75] Inventor: Thomas J. Schwan, Norwich, N.Y.

[73] Assignee: Morton-Norwich Products, Inc., Norwich, N.Y.

[22] Filed: Jan. 29, 1976

[21] Appl. No.: 653,447

[52] U.S. Cl. .................. 260/310 C; 260/311; 424/273
[51] Int. Cl.² ............ C07D 231/56; A61K 31/415
[58] Field of Search ............ 260/310 C, 311; 424/273

[56] References Cited

UNITED STATES PATENTS

| | | | |
|---|---|---|---|
| 3,133,081 | 5/1964 | Lafferty et al. | 260/310 C |
| 3,493,649 | 2/1970 | Massaroli | 424/273 |
| 3,520,901 | 7/1970 | Massaroli | 424/273 |
| 3,651,081 | 3/1972 | Sturm et al. | 260/310 C |
| 3,681,382 | 8/1972 | Gschwend | 260/310 C |
| 3,705,175 | 12/1972 | Magdanyi et al. | 260/310 C |
| 3,711,506 | 1/1973 | Wagner et al. | 260/310 C |

FOREIGN PATENTS OR APPLICATIONS

| | | | |
|---|---|---|---|
| 2,522,314 | 12/1975 | Germany | |
| 40-6231 | 3/1965 | Japan | 260/310 C |
| 42-5541 | 7/1967 | Japan | 260/310 C |

OTHER PUBLICATIONS

Chemical Abstracts, vol. 42:7538, (1948), vol. 65:1857g & vol. 80:44022q, (1974).

*Primary Examiner*—Donald B. Moyer
*Attorney, Agent, or Firm*—Anthony J. Franze

[57] ABSTRACT

3-Amino-5,6-dimethoxyindazole hydrochloride possesses pharmacological activity as a hypotensive agent.

1 Claim, No Drawings

3-AMINO-5,6-DIMETHOXYINDAZOLE HYDROCHLORIDE

This invention relates to a compound of the formula:

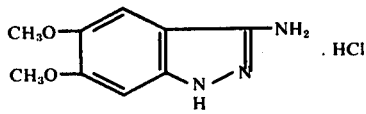

When administered intravenously to animals this compound exhibits hypotensive activity. Intravenous administration in physiologically acceptable menstrua of 25 and 50 mg/kg of this compound to anesthetized normotensive dogs resulted in decrease in blood pressure ranging from 68–80% for long duration (>4hr).

In order that this invention be readily available to and understood by those skilled in the art, the following illustrative example is included:

3-Amino-5,6-dimethoxyindazole hydrochloride

To a solution of 6-aminoveratronitrile (39 g, 0.2 mole) and conc. hydrochloric acid (329 ml) was added a solution of sodium nitrite (17 g, 0.25 mole in minimum amt. of water). The temperature was held below 0° during the addition. Keeping the temperature between 0° to 20° the resulting solution was added dropwise to stannous chloride (33.3 g, 1.76 mole) and conc. hydrochloric acid (153 ml). The precipitate was filtered and air dried overnight. The filter cake was placed in water (1100 ml), refluxed for 20–30 min and then filtered. The filtrate was cooled and then treated with sodium hydroxide (10% – 290 ml) to precipitate a tan solid. This solid was air dried at 60° to yield 57 g of 3-amino-5,6-dimethoxyindazole.

The free base was refluxed in 1700 ml of methanol and filtered hot. The filtrate was treated with methanolic hydrogen chloride to yield 30 g (65%) of the product, m.p. 274°–75°.

Anal. Calcd. for $C_9H_{11}N_3O_2 \cdot HCl$: C, 47.07; H, 5.27; N, 18.30. Found: C, 47.16; H, 5.49; H, 18.15.

What is claimed is:
1. The compound of the formula:

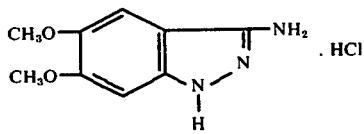

* * * * *